(12) United States Patent
Sharman et al.

(10) Patent No.: US 11,786,214 B2
(45) Date of Patent: Oct. 17, 2023

(54) ADJUSTABLE FLEXIBILITY STIFFNESS INTRALUMINAL DEVICE AND ASSOCIATED DEVICES SYSTEMS AND METHODS

(71) Applicant: KONINKLIJKE PHILIPS N.V., Eindhoven (NL)

(72) Inventors: Valerie Sharman, Oceanside, CA (US); Eve Lambert-Fliszar, San Diego, CA (US)

(73) Assignee: KONINKLIJKE PHILIPS N.V.

( * ) Notice: Subject to any disclaimer, the term of this patent is extended or adjusted under 35 U.S.C. 154(b) by 241 days.

(21) Appl. No.: 16/108,767

(22) Filed: Aug. 22, 2018

(65) Prior Publication Data

US 2019/0060613 A1    Feb. 28, 2019

Related U.S. Application Data

(60) Provisional application No. 62/548,881, filed on Aug. 22, 2017.

(51) Int. Cl.
*A61B 8/00* (2006.01)
*A61B 5/00* (2006.01)
*A61B 1/00* (2006.01)
*A61M 25/00* (2006.01)
(Continued)

(52) U.S. Cl.
CPC ........ *A61B 8/4466* (2013.01); *A61B 1/00078* (2013.01); *A61B 5/6852* (2013.01); *A61B 5/6876* (2013.01); *A61B 8/12* (2013.01); *A61M 25/0054* (2013.01); *A61M 25/0032* (2013.01);
(Continued)

(58) Field of Classification Search
CPC ..... A61B 8/026; A61B 5/6852; A61B 5/6876; A61B 8/44; A61B 8/4444; A61B 8/4466; A61B 1/00078; A61B 5/0215; A61B 5/026; A61B 1/00135; A61B 1/018; A61B 5/01; A61B 8/12; A61B 8/445; A61M 25/0026; A61M 25/0054; A61M 25/005; A61M 2205/103; A61M 25/00; A61M 25/014; A61M 25/0063; A61M 25/0002; A61M 2025/002; A61M 2025/0037; A61M 25/01; A61M 25/09041; A61M 2025/09083; A61M 2025/0002; A61M 2025/0063;
(Continued)

(56) References Cited

U.S. PATENT DOCUMENTS 6,551,302 B1   4/2003  Rosinko
7,846,101 B2   12/2010 Eberle et al.
(Continued)

FOREIGN PATENT DOCUMENTS

JP    2016059551 A    4/2016

*Primary Examiner* — Angela M Hoffa
*Assistant Examiner* — Younhee Choi

(57) ABSTRACT

An interventional device includes an elongate member configured to be inserted into a body of a patient, the elongate member comprising a proximal portion and a distal portion, a sensing element disposed at the distal portion of the elongate member and configured to obtain measurement data associated with a body lumen; a stiffening mechanism coupled to the elongate member and configured to change the stiffness of the elongate member during a medical procedure. Associated devices, systems and methods are also provided.

19 Claims, 8 Drawing Sheets

(51) Int. Cl.
  *A61B 8/12* (2006.01)
  *A61M 25/01* (2006.01)
(52) U.S. Cl.
  CPC . *A61M 25/0141* (2013.01); *A61M 2025/0063* (2013.01)
(58) Field of Classification Search
  CPC .......... A61M 25/0032; A61M 25/0141; B06B 1/0633
  See application file for complete search history.

(56) References Cited

U.S. PATENT DOCUMENTS

| | | | |
|---|---|---|---|
| 2003/0163085 A1* | 8/2003 | Tanner | A61M 25/0136 604/95.01 |
| 2005/0070844 A1 | 3/2005 | Chow et al. | |
| 2006/0235458 A1 | 10/2006 | Belson | |
| 2007/0021771 A1 | 1/2007 | Oepen et al. | |
| 2007/0038061 A1* | 2/2007 | Huennekens | A61B 8/12 600/407 |
| 2007/0060880 A1* | 3/2007 | Gregorich | A61M 25/0053 604/96.01 |
| 2007/0250036 A1 | 10/2007 | Volk et al. | |
| 2009/0163891 A1* | 6/2009 | Ewing | A61M 25/104 604/526 |
| 2010/0297334 A1* | 11/2010 | Weber | A61M 25/0054 427/2.25 |
| 2012/0123352 A1 | 5/2012 | Fruland | |
| 2012/0179097 A1 | 7/2012 | Cully | |
| 2012/0277729 A1* | 11/2012 | Melsheimer | A61M 25/0053 604/525 |
| 2013/0131644 A1* | 5/2013 | Parodi | A61B 17/1214 604/528 |
| 2014/0171736 A1 | 6/2014 | Stigall et al. | |
| 2014/0222047 A1* | 8/2014 | Vreeman | A61B 17/3207 606/159 |
| 2015/0258306 A1* | 9/2015 | Plassman | A61M 25/0053 604/527 |
| 2016/0279388 A1* | 9/2016 | Barrish | A61M 25/1034 |
| 2017/0056046 A1* | 3/2017 | Vreeman | A61B 17/00234 |

* cited by examiner

ADJUSTABLE FLEXIBILITY STIFFNESS INTRALUMINAL DEVICE AND ASSOCIATED DEVICES SYSTEMS AND METHODS

TECHNICAL FIELD

The present disclosure relates generally to structure of an intraluminal device, such as an intravascular catheter, used to obtain data (e.g., images, pressure measurements, flow measurements, etc.) associated with a lumen of a patient body. For example, the flexibility/stiffness of the body of the intraluminal device can be adjusted by a medical professional during a medical procedure.

BACKGROUND

Heart disease is very serious and often requires emergency operations. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

Intravascular diagnostic tools, such as intravascular ultrasound (IVUS) and intravascular pressure measurements are used for assessing a diseased vessel, such as an artery, within the human body to determine the need for treatment, to guide a therapeutic intervention, and/or to assess the effectiveness of the treatment. Manufacturing an intravascular device that can efficiently traverse different segments of anatomical structures within the human body is challenging because the flexibility/stiffness characteristics of conventional intravascular devices is typically fixed at manufacturing.

SUMMARY

Embodiments of the present disclosure provide an intraluminal device with an adjustable flexibility/stiffness during a medical procedure. For example, an intravascular catheter may be sized and shaped to be positioned within blood vessels of a patient. The intraluminal device may include sensing element that is operable to obtain intraluminal data (e.g., intravascular ultrasound (IVUS) images, pressure measurements, flow measurements, etc.) associated with a body lumen of the patient, such as the patient's blood vessels. The intraluminal device may include a stiffness modulator that allows a physician to change the flexibility/stiffness of the intraluminal device during the medical procedure. The stiffness modulator is used to adjust the flexibility/stiffness of the catheter in order to allow the intraluminal device to traverse different anatomical features of the patient's body. For example, the stiffness modulator can increase the flexibility of the intraluminal device in order to traverse tight turns and/or otherwise tortuous vasculature. The stiffness modular can increase the stiffness of the intraluminal device in order to cross an occlusion of the blood vessel. Advantageously, the same intraluminal device can be used to traverse different types of anatomical features that require different flexibility/stiffness characteristics.

According to aspects of the present disclosure intraluminal sensing device is provided. The intraluminal sensing device includes an elongate member configured to be inserted into a body lumen of a patient, the elongate member comprising a proximal portion and a distal portion; a sensing element disposed at the distal portion of the elongate member and configured to obtain intraluminal data associated with the body lumen; a stiffening mechanism coupled to the elongate member and configured change the stiffness of the elongate member during a medical procedure.

In some aspects, the sensing element comprises an imaging element. In some aspects, the imaging element comprises an intravascular ultrasound (IVUS) transducer. In some aspects, the elongate member comprises a catheter. In some aspects, the elongate member comprises a lumen extending from the distal portion to the proximal portion. In some aspects, the stiffening mechanism comprises a tensioning member extending along the elongated member and a stiffness modulator coupled to the tensioning member and disposed at the proximal portion of the elongate member. In some aspects, the tensioning member is disposed within the lumen. In some aspects, the stiffness modulator comprises a resilient mechanism disposed at a distal end of the stiffness modulator. In some aspects, the tensioning member extends through the resilient mechanism. In some aspects, the tensioning member is coupled to the biasing member. In some aspects, the biasing member is operable to translate axially and rotate within the stiffness modulator. In some aspects, the stiffness mechanism is configured to reduce the stiffness of the elongate member when the stiffness mechanism is in a first position. In some aspects, the stiffness mechanism is configured to reduce the stiffness of the elongate member when the stiffness mechanism is in a second position.

According to aspects of the present disclosure, a method is provided. The method includes positioning an intraluminal device within an anatomy of a patient, the intraluminal device comprises stiffening mechanism configured to change the stiffness of the elongate member during a medical procedure; moving the intraluminal device across a first feature of the anatomy; adjusting a flexibility of the intraluminal device using the stiffening mechanism; moving the intraluminal device across a second feature of the anatomy; and obtaining intraluminal data associated with the anatomy using a sensing element of the intraluminal device.

In some aspects, the method further comprises increasing flexibility of the intraluminal device using the stiffening mechanism. In some aspects, the method further comprises decreasing the flexibility of the intraluminal device using the stiffening mechanism. In some aspects, the method further comprises applying a compressive force to the resilient mechanism. In some aspects, the method further comprises applying a tensile force to a resilient mechanism.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
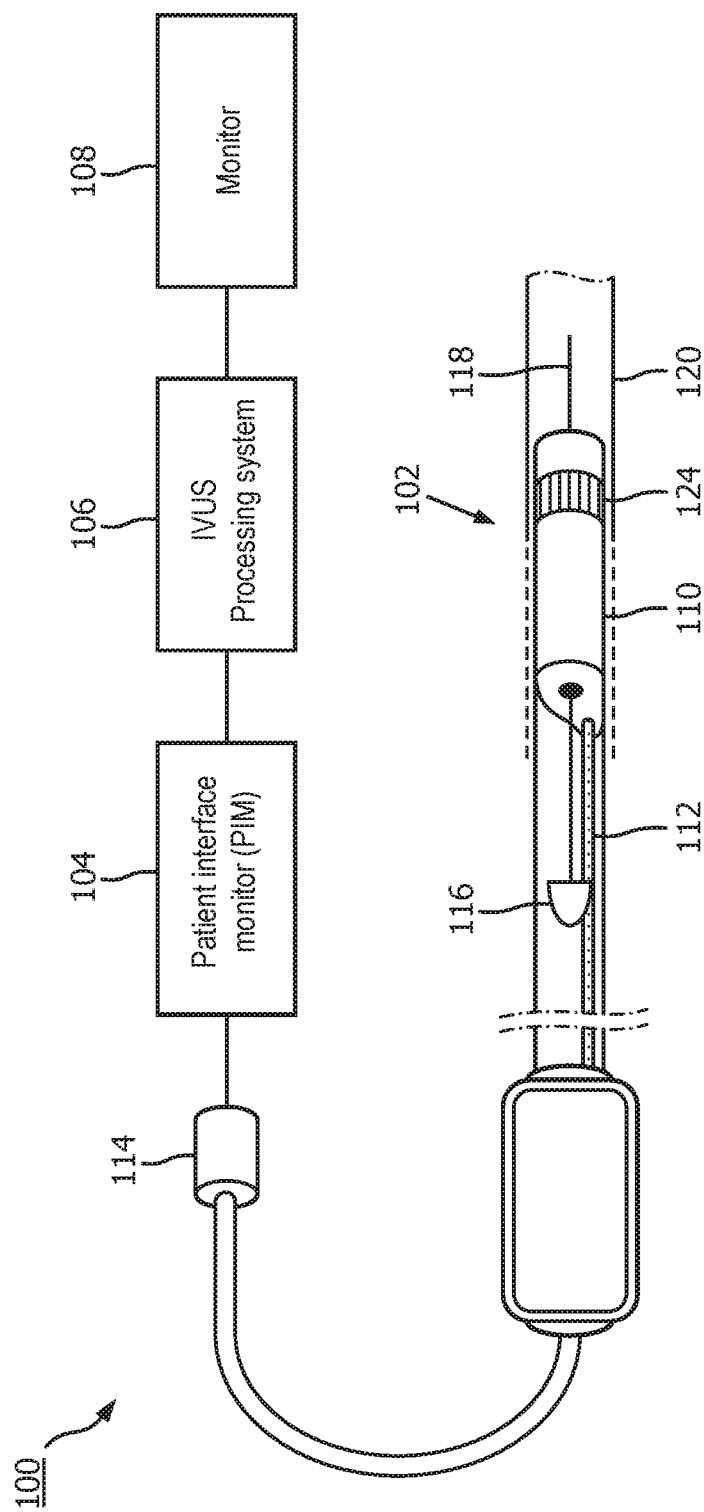
FIG. 1 is a diagrammatic schematic view of an intraluminal sensing system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal sensing system 100, according to aspects of the present disclosure. For example, the system 100 can be an intravascular ultrasound (IVUS) imaging system. The IVUS imaging system 100 may include a solid-state or phased array IVUS device 102, a patient interface module (PIM) 104, an IVUS processing system or console 106, and a monitor 108. The intraluminal device 102 can be any suitable structure, including a catheter, guide wire, or guide catheter.

At a high level, the IVUS device 102 emits ultrasonic energy from a transducer array 124 included in scanner assembly 110 mounted near a distal end of the catheter device. The ultrasonic energy is reflected by tissue structures in the medium, such as a body lumen and/or vessel 120, surrounding the scanner assembly 110, and the ultrasound echoes are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducers between 1 transducer and 1000 transducers, including values such as 2 transducers, 4 transducers, 36 transducers, 64 transducers, 128 transducers, 500 transducers, 812 transducers, and/or other values both larger and smaller.

The PIM 104 transfers the received echo signals to the console or computer 106 where the ultrasound image is reconstructed and displayed on the monitor 108. The console or computer 106 can a processing circuit, such as a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to an integrated circuit controller chip(s) included in the scanner assembly 110 to select the particular transducer array element(s) to be used for transmit and receive, (2) providing the transmit trigger signals to the integrated circuit controller chip(s) included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The console 106 outputs image data such that an image of the vessel 120, such as a cross-sectional IVUS image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more micro cables 244 (FIG. 2C). It is understood that any suitable gauge wire can be used for the micro cables 244. In an embodiment, the transmission line bundle 112 can include a four-conductor transmission line arrangement with, e.g., 41 AWG gauge wires. In an embodiment, the transmission line bundle 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. The guide wire exit port 116 can be provided at any longitudinal location along the device 102. For example, when the device 102 is an over-the-wire catheter, the exit port 116 can be provided at the proximal end of the device 102. When the device 102 is a rapid-exchange catheter, the exit port 116 can be provided at the distal portion of the device 102. Generally, the guide wire exit port 116 allows a guide wire 118 to be inserted within a lumen of the device 102, in order to direct the device 102 through the vessel 120.

While system 100 and/or device 102 have been described in the context of phased array IVUS imaging, it is understood that the system 100 and/or device 102 can be configured to obtain any suitable intraluminal sensing data. In various embodiments, the device 102 can obtain imaging data associated with intravascular ultrasound (IVUS) imaging, forward looking intravascular ultrasound (FL-IVUS) imaging, intravascular photoacoustic (IVPA) imaging, intracardiac echocardiography (ICE), transesophageal echocardiography (TEE), and/or other suitable imaging modalities. In some embodiments, the device 102 can include an imaging component of any suitable imaging modality, such as optical imaging, optical coherence tomography (OCT), etc. In some embodiments, the device 102 can include any suitable sensing component, including a pressure sensor, a flow sensor, a temperature sensor, an optical fiber, a reflector, a mirror, a prism, an ablation element, a radio frequency (RF) electrode, a conductor, and/or combinations thereof.

Figure 2A:
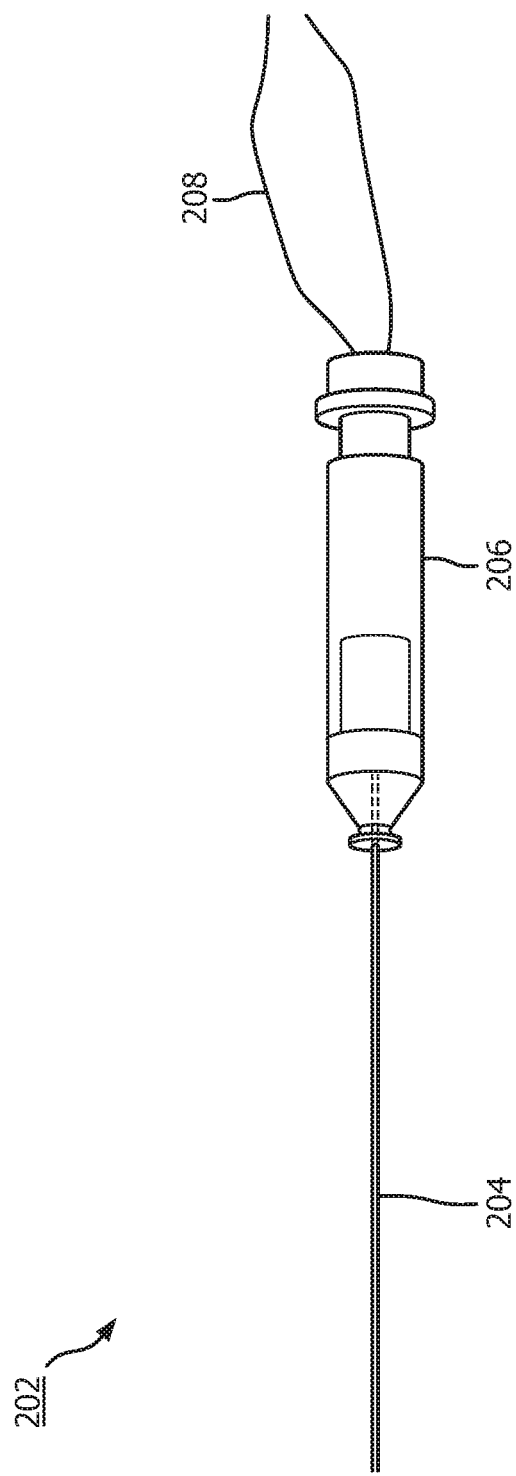
FIG. 2A is a diagrammatic top view of a rigidity modulating catheter, according to aspects of the present disclosure.
Figure 2B:
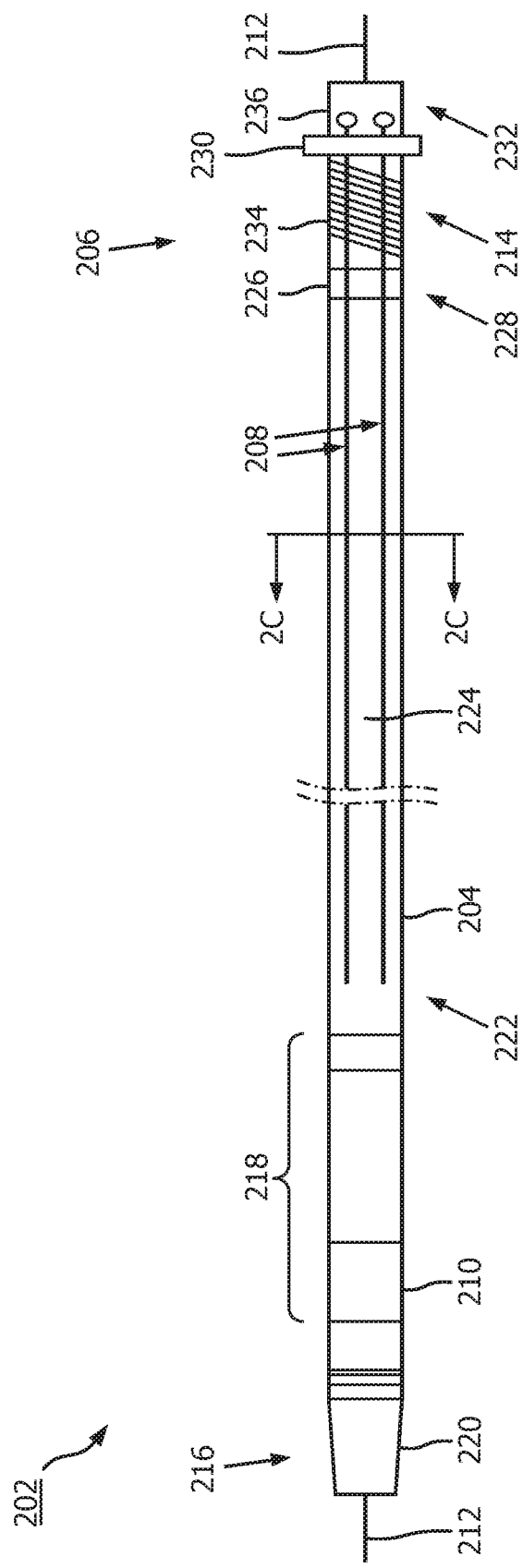
FIG. 2B is a diagrammatic cross-sectional top view of a rigidity modulating catheter, according to aspects of the present disclosure.
Figure 2C:
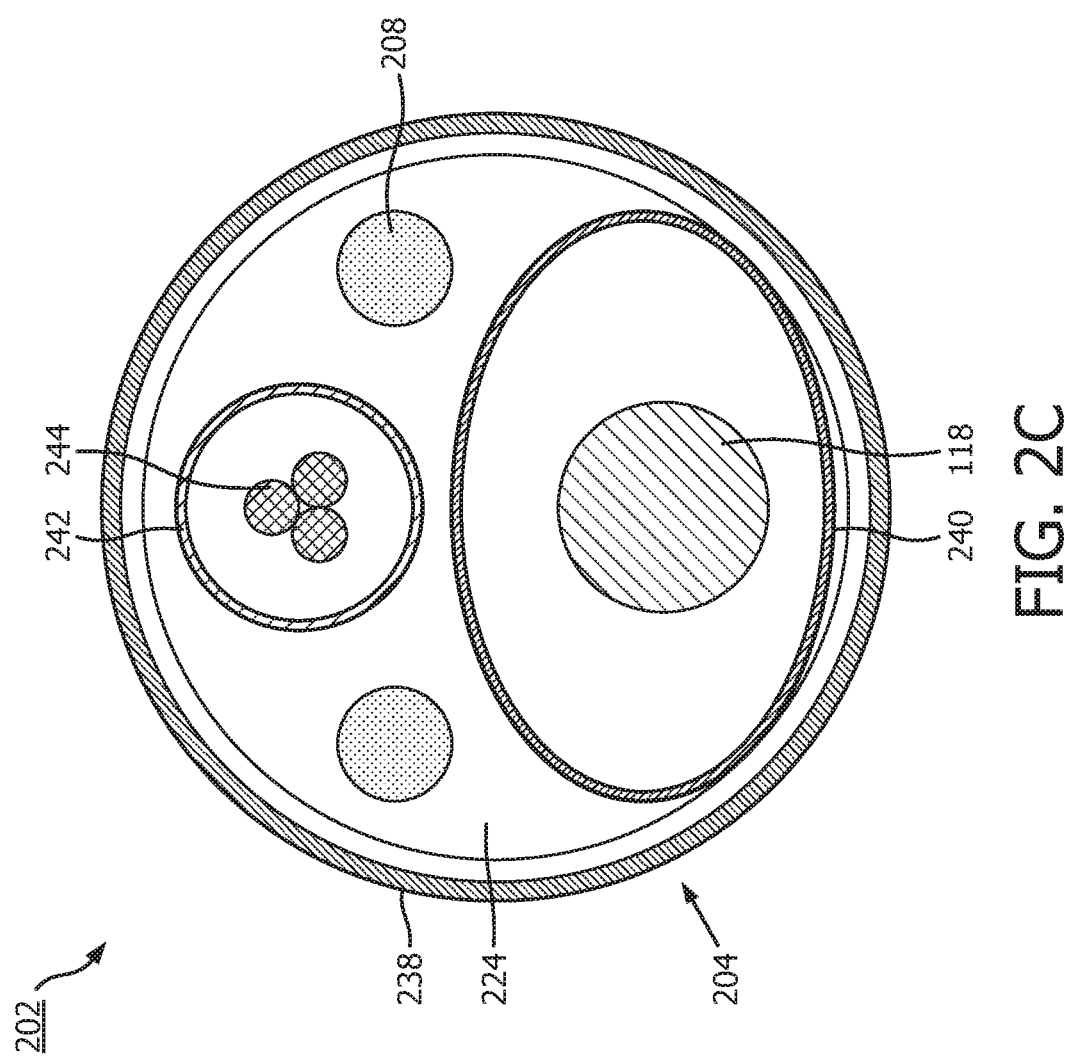
FIG. 2C is a diagrammatic cross sectional view of an elongated member of a rigidity modulating catheter along section line 2C-2C of FIG. 2B, according to aspects of the present disclosure.

FIGS. 2A and 2B present a top view and a top cross sectional view of an embodiment of the intraluminal device 102 of the system 100, respectively. As shown in FIG. 2A, the device 102 is a rigidity modulating catheter 202, which includes a compressible elongate member 204 and a stiffening mechanism, such as a stiffness modulator 206 and tensioning members 208. FIG. 2A provides an illustration of the relative size of the components of the rigidity modulating catheter 202 with respect to one another. As such, it will be appreciated that the compressible elongate member 204 is sized to be inserted into a vessel 120 of a patient while the stiffness modulator 206 is sized to be positioned outside of the patient. As described further herein, the stiffness modulator 206 functions to either increase or decrease of the flexibility/stiffness of the compressible elongate member 204, by applying or releasing tension on the tensioning members 208, which extend through the compressible elongate member 204 and the stiffness modulator 206. Generally, as described herein, the elongate member 204 can have varying flexibility/stiffness, based on the stiffness modulator 206 and/or the tensioning members 208. The elongate member 204 can be referenced as a compressible elongate member in some embodiments to describe its variable stiffness/flexibility.

FIG. 2B provides a top cross sectional view of the rigidity modulating catheter 202. The elongate member 204 and the stiffness modulator 206 are aligned along a longitudinal axis 212 that extends from a proximal portion 214 of the rigidity modulating catheter 202 to a distal portion 216 of the rigidity modulating catheter 202. In some embodiments, a guide wire can extend through the rigidity modulating catheter 202 along the longitudinal axis 212. In certain embodiments, the distal portion 216 of the rigidity modulating catheter 202 may include a sensing element 210 (e.g., similar to the scanner assembly 110 described with respect to FIG. 1), a transitional section 218, and a tip member 220. The transitional section 218 may be a shaft that is mechanically coupled a distal end 222 of the compressible elongate member 204. The transitional section 218 may be constructed from any number of flexible materials that, along with the tip member 220 functions to facilitate traversing various types of radii and obstructions encountered in the anatomy of a patient. The material and geometry of the transitional section 218 and the tip member may be tailored for any specific application. In some embodiments, the sensing element 210 can be a rigid portion of the elongate member 204. The transitional section 218 is structurally arranged to allow transition between the rigidity of the sensing element 210 and the stiffness/flexibility of more proximal portions of the elongate member 204. For example, the durometer hardness of one or more materials of the transitional section 218 can be selected to eliminate kink points at or proximal to the sensing element 210.

The elongate member 204 may include a coiled shaft defining a main lumen 224 extending therethrough. Alternatively, the elongate member 204 may be comprised of any another compressible metal or plastic shaft. As used herein, "elongate member" includes at least any thin, long structure structurally arranged (e.g., sized and/or shaped) to be positioned within a lumen of the vessel 120. For example, a distal portion 216 of the elongate member 204 is positioned within the vessel 120, while a proximal portion 214 of the elongate member 204 is positioned outside of the body of the patient. The elongate member 204 can include a longitudinal axis 212. In some instances, the longitudinal axis 212 can be a central longitudinal axis of the elongate member 204. In some embodiments, the elongate member 204 can include one or more polymer/plastic layers formed of various grades of nylon, Pebax, polymer composites, polyimides, and/or Teflon. In some embodiments, the elongate member 204 can include one or more layers of braided metallic and/or polymer strands. The braided layer(s) can be tightly or loosely braided in any suitable configuration, including any suitable per in count (pic). In some embodiments, the elongate member 204 can include one or more metallic and/or polymer coils. All or a portion of the elongate member 204 may have any suitable geometric cross-sectional profile (e.g., circular, oval, rectangular, square, elliptical, etc.) or non-geometric cross-sectional profile. For example, the elongate member 204 can have a generally cylindrical profile with a circular cross-sectional profile that defines an outer diameter of the elongate member 204. For example, the outer diameter of the elongate member 204 can be any suitable value for positioning within the vessel 120, including between approximately 1 Fr (0.3 mm) and approximately 15 Fr (5 mm), including values such as 3.5 Fr, 5 Fr, 7 Fr, 8.2 Fr, 9 Fr, and/or other suitable values both larger and smaller.

The compressible elongate member 204 and the stiffness modulator 206 are mechanically coupled at the proximal portion 214 of the rigidity modulating catheter 202 by any mechanical apparatus or method. Although FIG. 2B illustrates the compressible elongate member 204 containing two tensioning members 208, it is anticipated that more or fewer tensioning members 208 may be used. For example, one, two, three, four, five, six, or more tensioning members 208 can be implemented in the rigidity modulating catheter 202. The tensioning members 208 may include a tensile pre-load, which may be determined based upon desired a range of flexibility for the rigidity modulating catheter 202. In an embodiment, the tensioning members 208 may be disposed within and affixed to the inner wall of the main lumen 224 of the compressible elongate member 204. The tensioning members 208 may be coupled to the lumen 224 using an adhesive or suspended within using reflowed polymer. Alternatively, the tensioning members 208 may be coupled to the inner wall of the main lumen 224 using other mechanical apparatuses or methods. The tensioning members 208 are coupled to the inner wall of the main lumen 224 at one end and as discussed further herein, coupled to stiffness modulator 206 at the other end. In an embodiment, the tensioning members 208 may be any type of filar such as a thread, cord, fiber or line which has a high tensile strength to weight ratio. For instance the tensioning members 208 may be comprised of aramid materials such as KEVLAR® (registered trademark of E.I. du Pont) or TECHNORA® (registered trademark of Eurofibers).

The stiffness modulator 206 may be disposed at the proximal portion 214 of the rigidity modulating catheter 202. In an embodiment, the stiffness modulator 206 may contain a fixed member 226, disposed at a distal end 228 of the stiffness modulator 206 and a biasing member 230 disposed at a proximal end 232 of the stiffness modulator 206. Disposed between the fixed member 226 and the biasing member 230 is a resilient mechanism 234, which is coupled to the biasing member 230 and in contact with the fixed member 226. In an embodiment, the resilient mechanism 234 may be a spring or any other elastic object that is used to store mechanical energy.

As shown in FIG. 2B, the tensioning members 208 extend through the fixed member 226, the resilient mechanism 234 and the biasing member 230 to which the tensioning members 208 are coupled under tension. In some instances, the tensioning members may comprise a head 236, which is configured to be attached to the biasing member 230. The head 236 of the tensioning members 208 may be attached to the biasing member 230 by using an adhesive or tying the tensioning members 208 to the biasing member 230. However, it is anticipated that the tensioning members 208 may be attached to the biasing member by other mechanical methods or apparatuses. As the elastic tensioning members 208 are coupled to the compressible elongate member 204 and the biasing member 230 of the stiffness modulator 206 under tension, it will be appreciated that actuation of the biasing member 230 will result in either an increase or decrease of the stiffness of the compressible elongate member 204 and thereby the rigidity modulating catheter 202. For instance, as the biasing member 230 is coupled to both the tensioning members 208 and the resilient mechanism 234, application of a tensile force, large enough to overcome the force of the resilient mechanism 234 at equilibrium, to the biasing member 230 causes the biasing member 230 to translate towards the proximal end 232 of the stiffness modulator 206, which results in the elongation of both the tensioning members 208 and the resilient mechanism 234. The elongation of the tensioning members 208 causes the stiffness of the compressible elongate member 204 to increase, which as discussed further herein may be advantageous in traversing the rigidity modulating catheter 202 through an occlusion, without substantially changing the shape of the elongate member 2014 from its neutral position. There is no substantial steering effect of the distal portion of the elongate member due to movement of the tensioning members. Conversely, application of a compressive force, large enough to overcome the force of the resilient mechanism 234 at equilibrium, to the biasing member 230 causes the biasing member 230 to translate towards the distal end 228 of the stiffness modulator 206, which results in the compression of both the tensioning members 208 and the resilient mechanism 234. The compression of the tensioning members 208 causes the stiffness of the compressible elongate member 204 to decrease, which, as discussed further herein may be advantageous in traversing the rigidity modulating catheter 202 through a vessel 120 with a bending radius.

FIG. 2C presents a cross sectional view of the elongate member 204 of the rigidity modulating catheter 202. In this embodiment, the rigidity modulating catheter 202 includes a sleeve 238 disposed around the compressible elongate member 204. The sleeve 238 is configured to prevent the compressible elongate member 204 from becoming caught or stuck on the anatomy of a patient when modulating from a flexible state to a rigid or less flexible state or traversing the anatomy of the patient. As such, in some embodiments, the sleeve 238 may be comprised of a polymer jacket. A hydrophilic coating can be provided on or outside of the sleeve 238. Although FIG. 2C depicts the cross section of the elongate member 204 as circular, it will be appreciated that the cross section of the elongate member 204 may be configured to contain any polygonal or curvilinear cross section and may transition from one to another along the longitudinal axis 212 of the rigidity modulating catheter 202.

With continued reference to FIG. 2C, the main lumen 224 of the elongate member 204 may further include any number of additional lumens of varying geometrical shapes and sizes. In an embodiment, one of the additional lumens may be a guide wire lumen 240, which functions to facilitate movement of the rigidity modulating catheter 202 along the guide wire 118 within the vessel 120. Further, the main lumen 224 may include a micro cable lumen 242, which functions to house the power and communication micro cables 244 (e.g., see the transmission bundle 112 as described with respect to FIG. 1) that may extend through the rigidity modulating catheter 202 to the scanner assembly 110 (e.g., FIG. 1).

Figure 3A:
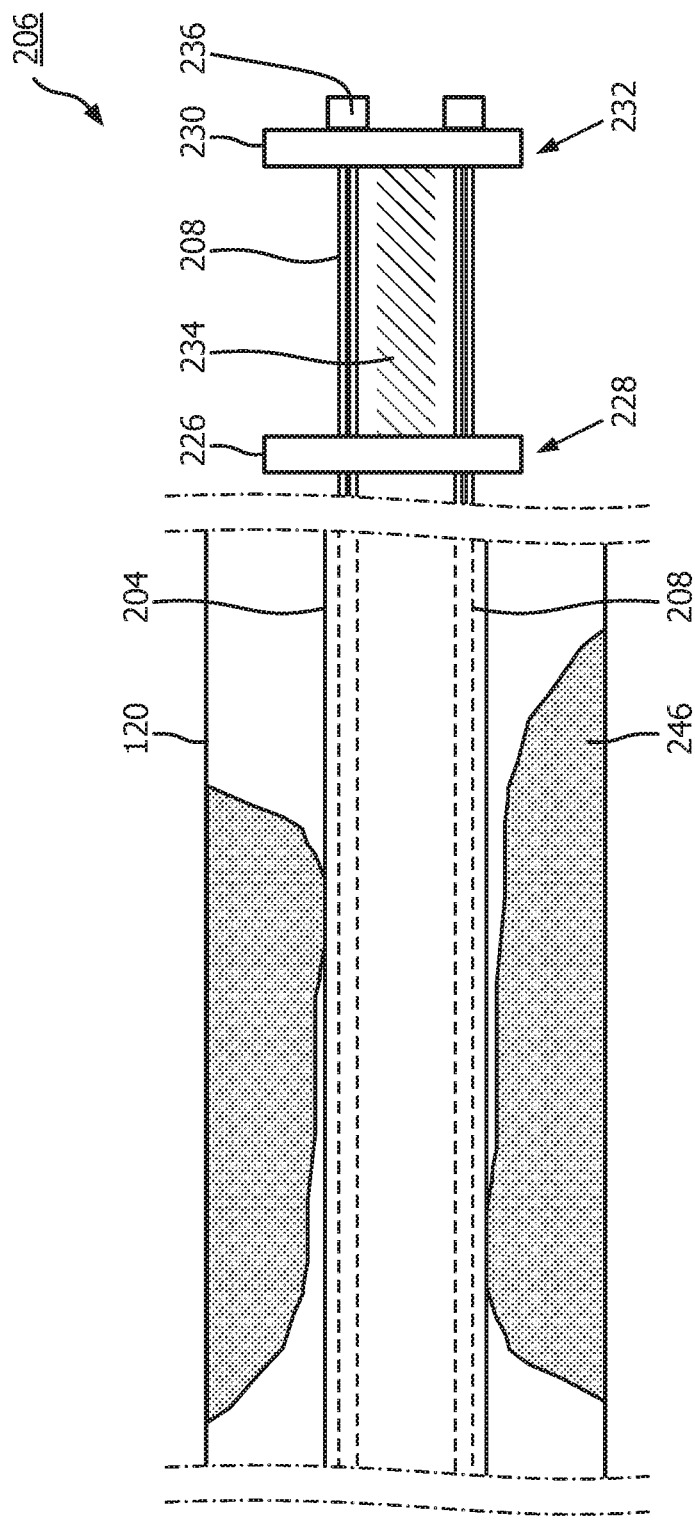
FIG. 3A is a diagrammatic cross sectional side view of a rigidity modulating catheter in a rigid configuration traversing an anatomy of a patient, according to aspects of the present disclosure.

FIG. 3A depicts the compressible elongate member 204 and the stiffness modulator 206 of the rigidity modulating catheter 202 when the rigidity modulating catheter 202 is in a rigid state. As previously discussed, the elastic tensioning members 208 are coupled under tension to the compressible elongate member 204 and the biasing member 230 of the stiffness modulator 206. Applying a tensile force to the biasing member 230 causes the biasing member 230 to longitudinally translate away from the fixed member 226 towards the proximal end 232 of the stiffness modulator 206. This translation results in the elongation of both the tensioning members 208 and the resilient mechanism 234 as the biasing member 230 is coupled to both the tensioning members 208 and the resilient mechanism 234. The elongation of the tensioning members 208 causes the stiffness of the compressible elongate member 204 to increase in proportion to the positive change in length of the resilient mechanism 234. In other terms, as the tensile force applied by the biasing member 230 to the resilient mechanism 234 increases, the stiffness of the compressible elongate member 204 also increases making it and the rigidity modulating catheter 202 rigid. The rigid compressible elongated member 204 maybe advantageously used to traverse the rigidity modulating catheter 202 through an occlusion 246 of the vessel 120. Traversing an occlusion requires the elongate member 204 have to more rigidity, as the device 102 is pushed through narrowing of body lumen caused by the occlusion 246. For example, the occlusion 246 can be blockage of a blood vessel, such as a chronic total occlusion (CTO).

The occlusion 246 of the vessel 120 is generally representative of any blockage or other structural arrangement that results in a restriction to the flow of fluid through the body lumen, for example, in a manner that is deleterious to the health of the patient. For example, the occlusion 246 narrows the lumen such that the cross-sectional area of the lumen and/or the available space for fluid to flow through the lumen is decreased. Where the anatomy 120 is a blood vessel, the occlusion 246 may be a result of plaque buildup, including without limitation plaque components such as fibrous, fibro-lipidic (fibro fatty), necrotic core, calcified (dense calcium), blood, fresh thrombus, and/or mature thrombus. In some instances, the occlusion 246 can be referenced as thrombus, a stenosis, and/or a lesion. Generally, the composition of the occlusion 246 will depend on the type of anatomy being evaluated. Healthier portions of the vessel 120 may have a uniform or symmetrical profile (e.g., a cylindrical profile with a circular cross-sectional profile). The occlusion 246 may not have a uniform or symmetrical profile. Accordingly, diseased portions of the vessel 120, with the occlusion 246, will have a non-symmetric and/or otherwise irregular profile. While the occlusion 246 is illustrated in FIG. 3A as having a single occlusion 246, it is understood that the devices, systems, and methods described herein have similar application for anatomy having multiple occlusions.

Figure 3B:
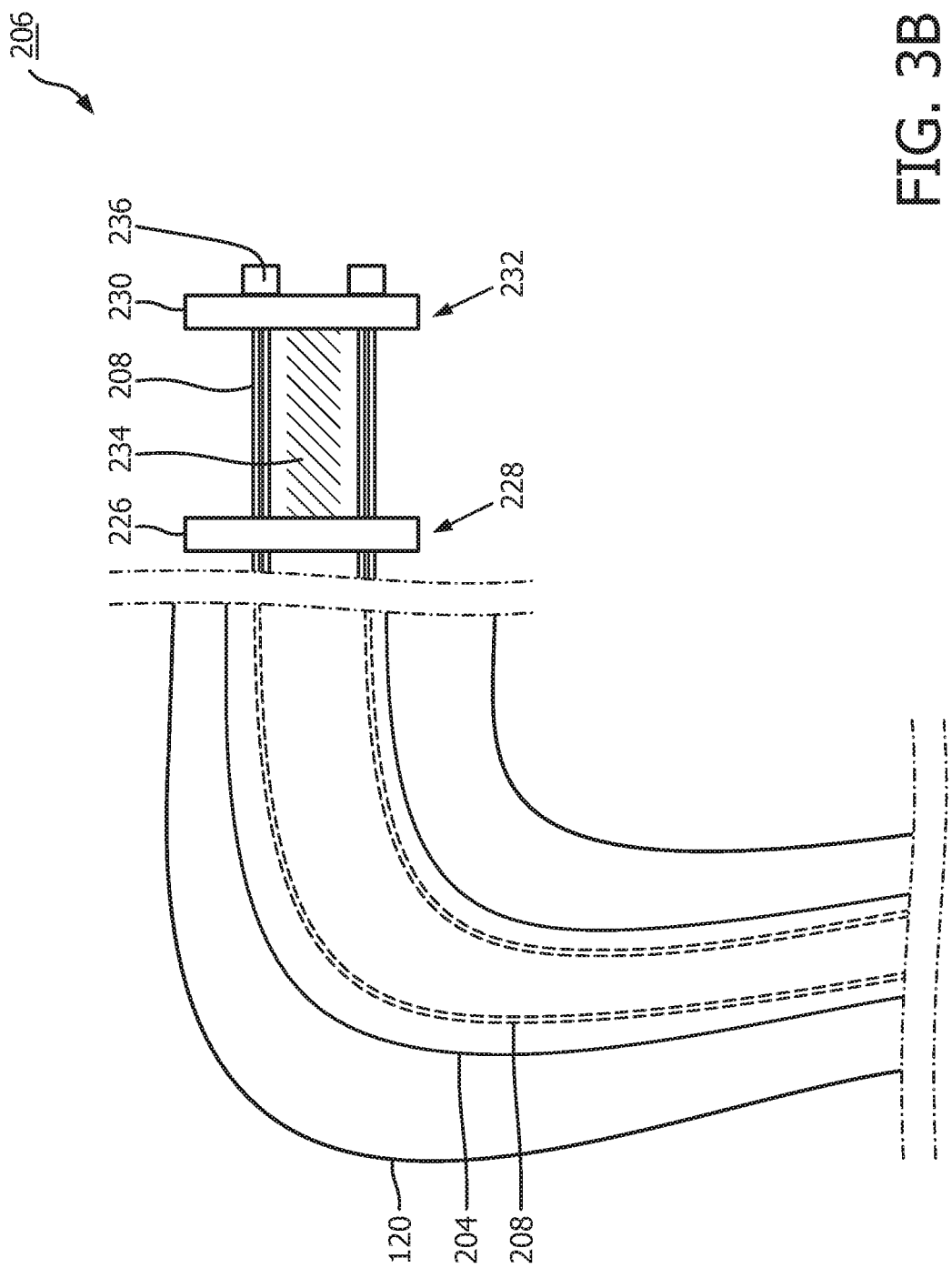
FIG. 3B is a diagrammatic cross sectional side view of a rigidity modulating catheter in a flexible configuration traversing an anatomy of a patient, according to aspects of the present disclosure.

FIG. 3B depicts the compressible elongate member 204 and the stiffness modulator 206 of the rigidity modulating catheter 202 when the rigidity modulating catheter 202 is in a flexible state. As the elastic tensioning members 208 are coupled under tension to the compressible elongate member 204 and the biasing member 230 of the stiffness modulator 206, it follows that the application of a compressive force to the biasing member 230 will have an opposite effect on the rigidity modulating catheter 202 from that of applying a tensile force. Applying a compressive force to the biasing member 230 causes the biasing member 230 to translate towards the distal end 228 of the stiffness modulator 206. This results in the compression of the resilient mechanism 234 against the fixed member 226 of the stiffness modulator 206 and the compression of tensioning members 208. The compression of the tensioning members 208 causes the stiffness of the compressible elongate member 204 to decrease in proportion to the negative change in length of the resilient mechanism 234. In other terms, as the compressive force applied by the biasing member 230 to the resilient mechanism 234 increases, the stiffness of the compressible elongate member 204 decreases allowing it to become more flexible. The flexible compressible elongate member 204 maybe advantageously used to traverse the rigidity modulating catheter 202 through a vessel 120 with a bending radius.

Figure 4:
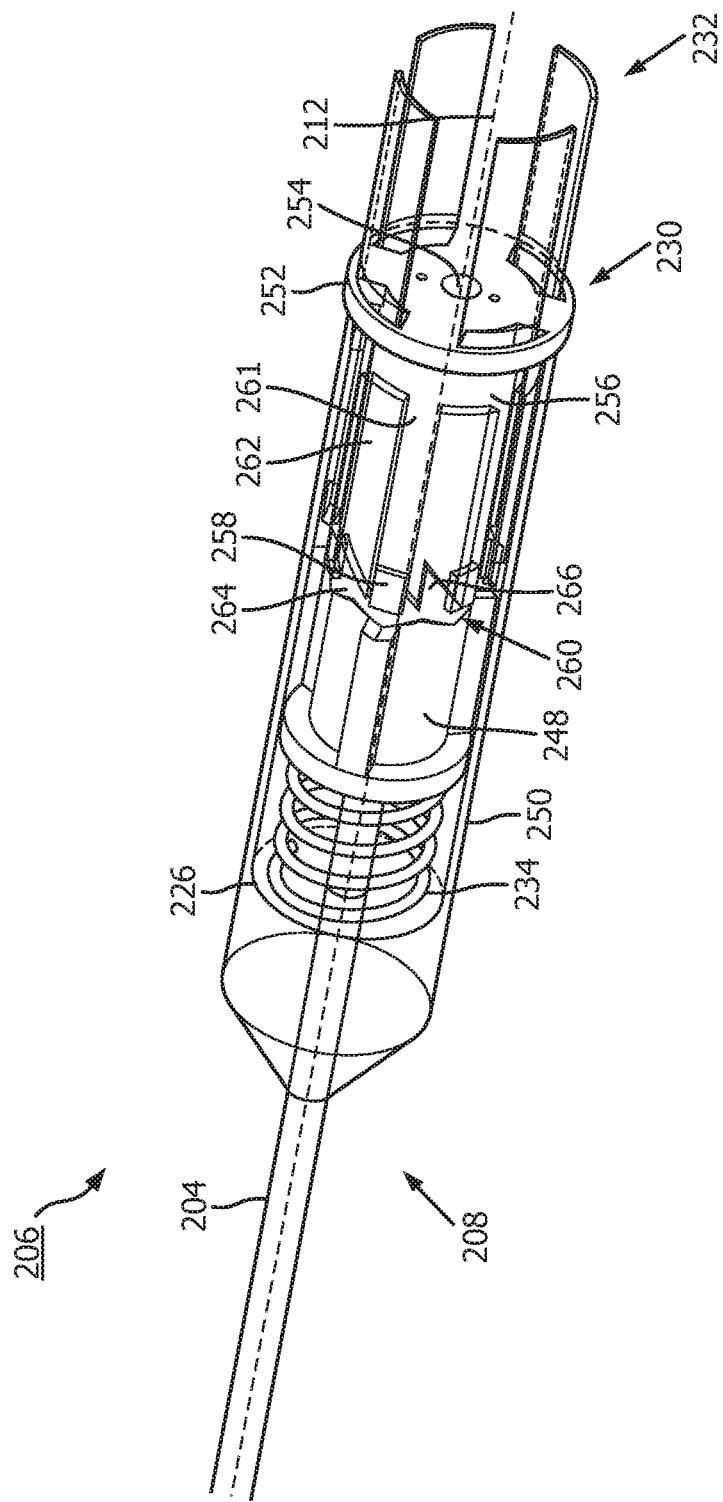
FIG. 4 is a diagrammatic perspective view of a stiffness modulator of a rigidity modulating catheter, according to aspects of the present disclosure.

FIG. 4 depicts diagrammatic perspective view of an embodiment of the stiffness modulator 206 and the compressible elongate member 204 of the rigidity modulating catheter 202. In this embodiment, the stiffness modulator 206 includes a biasing member 230, an intermediate member 248, a resilient mechanism 234 and a fixed member 226, which are each either completely or partially disposed within a shaft 250 that is mechanically coupled to the compressible elongate member 204.

The biasing member 230 may be comprised of a head member 252 having a plurality of apertures 254. Although three apertures are shown in FIG. 4, it is anticipated that more or fewer apertures 254 may be used. The apertures 254 may function to allow the tensioning members 208 and/or the guide wire 118 to be routed through the stiffness modulator 206, including the biasing member 230, towards the distal portion 216 of the rigidity modulating catheter 202 (e.g., FIG. 2B). In an embodiment, the head member 252 may be configured with apertures that function to facilitate the routing of a plurality of micro cables 244 through the stiffness modulator 206.

The biasing member 230 may further include a shaft member 256, which is coupled to the head member 252. FIG. 4 depicts the head member 252 and the shaft member 256 of the biasing member 230 as being integrated into one component. However, it will be appreciated that head member 252 and the shaft member 256 may be comprised of multiple separate components. A plurality of protrusions 258 may be spaced apart about the periphery of the shaft member 256 at a distal end 260. The protrusions 258 of the shaft member 256 are configured to translate axially along a track 261, which is defined between a set of rails 262 that are spaced apart about the inner wall of the shaft 250 of the stiffness modulator 206. At the distal end 264 of each rail 262 is a groove 266. As discussed further herein, the protrusions 258 are configured to engage the groove 266 of the rail 262 during the operation of the stiffness modulator 206.

In some instances, an intermediate member 248 is disposed between the biasing member 230 and the resilient mechanism 234. The intermediate member 248 is operable to axially transmit a force to both the biasing member 230 and the resilient mechanism 234. In some embodiments, the intermediate member 248 is shaped to correspondingly engage with the shape of the distal end 260 of the shaft member 256. The intermediate component 248 may be configured to translate axially within the shaft 250 of the stiffness modulator 206. In some embodiments, the intermediate component 248 may be configured to rotate and axially translate. While only one intermediate component 248 is shown in FIG. 4, it is understood in some embodiments that multiple intermediate components are implemented in the stiffness modulator 206 (e.g., one intermediate component each at the proximal and distal portions of the resilient mechanism 234).

To reduce the stiffness of the rigidity modulating catheter 202 using the embodiment of the stiffness modulator 206 as shown in FIG. 4, a compressive force, large enough to overcome the force of the resilient mechanism 234 at equilibrium is initially applied to the biasing member 230. The compressive force causes the shaft member 256 and protrusions 258 of the biasing member 230 to translate axially along the shaft 250 and the tracks 261 defined by the rails 262 of the stiffness modulator 206, respectively. Further, the compressive force causes the distal end 260 of the shaft member 256 to engage the intermediate member 248, which in turn engages and applies a compressive axial force to the resilient mechanism 234 against the fixed member 226. When the protrusions 258 reach the distal end 264 of the rails 262, a rotational force is the applied to the biasing member 230, which results in a partial revolution of the shaft member 256 and the protrusions 258. In some embodiments, the rotational force is applied as a result of the shape of the intermediate member 248 and the shape of the distal end 260 of the shaft member 256. In other embodiments, a user applies the rotational force. The partial revolution of the shaft member 256 caused by the rotational force results in the protrusions 258 to engaging the grooves 266 of the rail 262, thereby maintaining the compressive force on the intermediate member 248. As previously discussed with respect to FIG. 3B, when the resilient mechanism 234 is compressed against the fixed member 226 of the stiffness modulator 206 the tensioning members 208 are also in compression, which causes the stiffness of the compressible elongate member 204 to decrease thereby making the rigidity modulating catheter 202 flexible.

In order to increase the stiffness of the rigidity modulating catheter from a flexible state using the stiffness modulator 206 as shown in FIG. 4, a compressive force is initially applied to the biasing member 230 to disengage the protrusions 258 from the grooves 266 of the rail 262. Subsequently, a rotational force is applied to the biasing member 230, which results in a partial revolution of the shaft member 256 and the protrusions 258 causing the protrusions 258 to engage a track 261, which are defined by a set of rails 262 of the stiffness modulator 206. In some embodiments, the rotational force is applied as a result of the shape of the intermediate member 248 and the shape of the distal end 260 of the shaft member 256. In other embodiments, a user applies the rotational force. Once the protrusions 258 engage the track 261, the resilient mechanism 234 simultaneously exerts an axial force on the intermediate member 248, which in turn exerts the force on the shaft member 256 of the biasing member 230 translating the biasing member 230 towards the proximal end 232 of the stiffness modulator 206. As previously discussed with respect to FIG. 3A, when the biasing member 230 is translated towards the proximal end 232 of the stiffness modulator 206, the tensioning members 208 become elongated, which causes the stiffness of the compressible elongate member 204 to increase, thereby making the rigidity modulating catheter 202 rigid. The inner wall of the shaft 250 of the stiffness modulator 206 may comprise grooves that communicate with the rails 262, in which the protrusions 258 can engage for maintaining the tensile force on the tensioning members 208. In an embodiment the inner wall of the shaft 250 comprises multiple sets of grooves along its length in which the protrusions 258 can engage for maintaining a predetermined tension or compression force on the tensioning member 208 and/or the intermediate member 248. The location of the grooves along the shaft may be equally spaced or at various distances depending on the predetermined force required for the tensioning members 208 for providing appropriate stiffness of the elongate member 204 for traversing various segments of the lumen of the vessel 120.

In some embodiments, the biasing member 230 comprises a twist and lock mechanism. For example, to increase flexibility of the catheter, a user may first apply an axial force on the biasing member 230 (e.g., moving the biasing member distally) to compress the resilient mechanism 234, and then a rotational force on the biasing member 230 to twist and lock the biasing member 230 in position. The shaft 250 can be shaped to include a retention feature that locations the biasing member 230 in place. For example, to decrease flexibility of the catheter, a user may unlock the biasing member 230 by applying a rotational force on the biasing member 230 and then allow the resilient mechanism 234 to return to an equilibrium state (e.g., moving the biasing member proximally) to un-compress the resilient mechanism 234.

Figure 5:
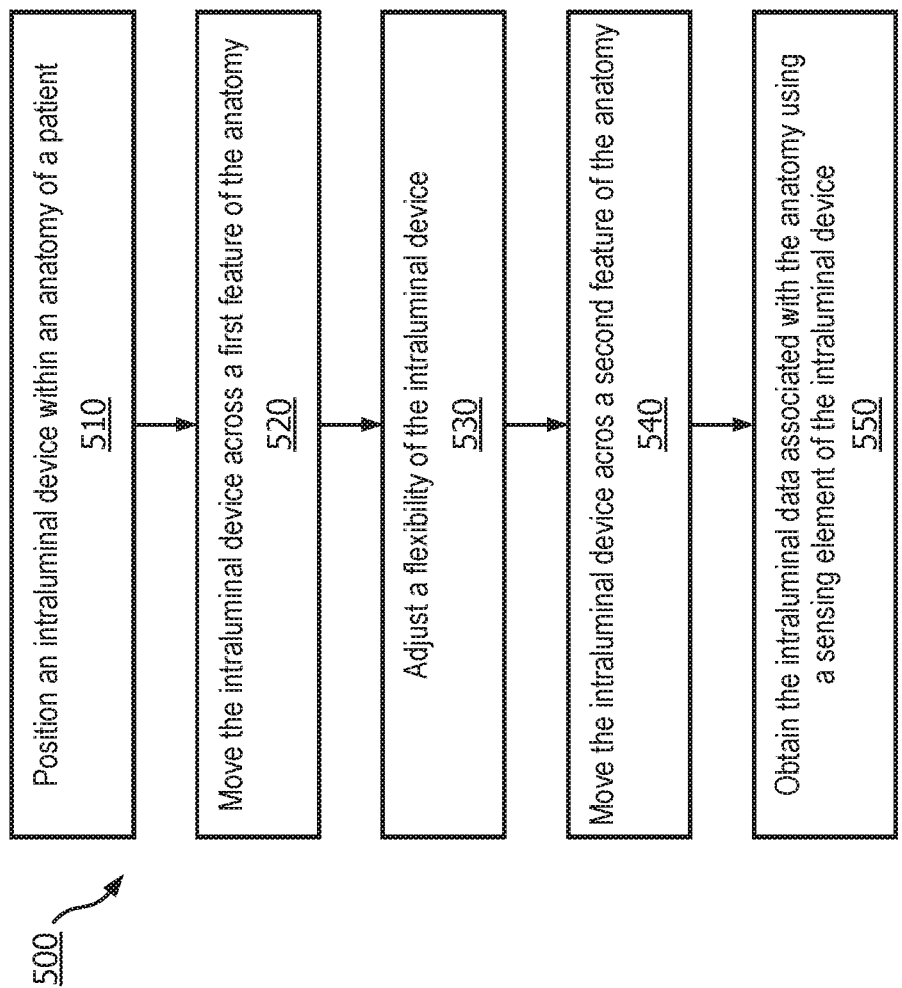
FIG. 5 is a flow diagram of a method for traversing various anatomies of a patient, according to aspects of the present disclosure.

FIG. 5 is a flow diagram of a method 500 for traversing various anatomies of a patient using an intraluminal sensing system and/or intraluminal device, such as those described herein. It is understood that the steps of method 500 may be performed in a different order than shown in FIG. 5, additional steps can be provided before, during, and after the steps, and/or some of the steps described can be replaced or eliminated in other embodiments. The steps of the method 500 can be carried out by a manufacturer of the intravascular imaging device.

Method 500 begins in step 510 by positioning an intraluminal device within an anatomy 120 of a patient. A guide wire 118 extending through a guide wire lumen 240 of the rigidity modulating catheter 202, may be used to position the rigidity modulating catheter 202 at desired location within a vessel 120 of the patient.

At step 520, the method 500 includes moving the intraluminal device across a first feature of the anatomy. For example, the first feature may be an occlusion or a bend in the patient's blood vessel. The intraluminal device can have a variable stiffness. The method 500 can include adjusting the stiff of the intraluminal device. For example, the stiffness can be increased (flexibility decreased) in order to traverse an occlusion. For example, the stiffness can be decreased (flexibility increase) in order to traverse a bend in the blood vessel. The stiffness can be selected such that the intraluminal device is able to cross the first feature.

At step 530, the method 500 includes adjusting a flexibility of the intraluminal device. The stiffness of the intravascular ultrasound imaging system 100 may be adjusted using the rigidity modulating catheter 202. In an embodiment, the rigidity modulating catheter 202 may include tensioning members 208, a compressible elongate member 204, and a stiffness modulator 206, which may include a fixed member 226, a resilient mechanism 234 and a biasing member 230. The elastic tensioning members 208 are coupled under tension to the compressible elongate member 204 and the biasing member 230 of the stiffness modulator 206.

For example, the flexibility of the intraluminal device can be adjusted in preparation for crossing a second feature of the anatomy that requires the intraluminal device to have different flexibility/stiffness characteristics. For example, when the first feature is an occlusion, the stiffness of the catheter is relatively higher is step 520. In step 530, the stiffness can be decreased (flexibility increased) in order to traverse a second feature, such as a bend in the blood vessel. For example, when the first feature is a bend in the blood vessel, the stiffness of the catheter is relatively lower is step 520. In step 530, the stiffness can be increased (flexibility decreased) in order to traverse a second feature, such as an occlusion in the blood vessel. In that regard, the step 530 can be performed by a medical professional during the medical procedure. In some embodiments, the step 530 can be performed while the intraluminal device is inside of the body lumen of the patient. In some embodiments, the step 530 can be performed within the procedure room, while the intraluminal device is outside of the patient.

In the event an occlusion 246 is encountered, it may be desirable to increase the stiffness of the ultrasound imaging system 100 using the rigidity modulating catheter 202. To accomplish this, a tensile force, large enough to overcome the force of the resilient mechanism 234 at equilibrium, may be applied to the biasing member 230, which causes the biasing member 230 to longitudinally translate away from the fixed member 226 towards a proximal end 232 of the stiffness modulator 206. This translation results in the elongation of both the tensioning members 208 and the resilient mechanism 234 as the biasing member 230 is coupled to both the tensioning members 208 and the resilient mechanism 234. Therefore, as the tensile force applied by the biasing member 230 to the resilient mechanism 234 increases, the stiffness of the compressible elongate member 204 also increases making the rigidity modulating catheter 202 rigid.

In the event a vessel 120 with a bending radius is encountered, it may be desirable to decrease the stiffness of the ultrasound imaging system 100 using the rigidity modulating catheter 202. To accomplish this, a compressive force, large enough to overcome the force of the resilient mechanism 234 at equilibrium may be applied to the biasing member 230. As previously discussed, the elastic tensioning members 208 are coupled under tension to the compressible elongate member 204 and the biasing member 230 of the stiffness modulator 206. Therefore, it follows that the application of a compressive force to the biasing member 230 will have an opposite effect on the rigidity modulating catheter 202 from that of applying a tensile force. Applying a compressive force to the biasing member 230 causes the biasing member 230 to translate towards a distal end 228 of the stiffness modulator 206. This results in the compression of the resilient mechanism 234 against the fixed member 226 of the stiffness modulator 206 and the compression of tensioning members 208. Accordingly, as the compressive force applied by the biasing member 230 to the resilient mechanism 234 increases, the stiffness of the compressible elongate member 204 decreases, making the rigidity modulating catheter 202 flexible.

At step 540, the method 500 includes moving the intraluminal device across the second features of the anatomy, based on the adjusted stiffness in step 530.

At step 550, the method 500 includes obtain intraluminal data associated with the anatomy using a sensing element of the intraluminal device. For example, the intraluminal data can be imaging data, pressure data, flow data, temperature data, etc. In some embodiments, the sensing element is a scanner assembly 110 of the intravascular ultrasound imaging system 100. The imaging data obtained by the scanner assembly 110 is used to create an image of the anatomy. For example, the scanner assembly 110 generates and emits ultrasound energy into the vessel 120 in response to transmission of an electrical signal to the scanner assembly 110. For imaging, the scanner assembly 110 generates and transmits an electrical signal representative of the received reflected ultrasound echoes from the vessel 120 (e.g., to the PIM 104 and/or IVUS processing system 106), which may be displayed as an ultrasound image on the monitor 108. In some embodiments, the ultrasound image is performed before the steps 520, 530, 540. In such embodiments, the obtained imaging data can used to determine the necessary degree of stiffness/flexibility needed to cross the first feature and/or the second feature of the anatomy. For example, the ultrasound image of the vessel 120 generated by the scanner assembly 110 is evaluated using virtual histology (VH) or other algorithms to determine whether an occlusion 246 is present or the nature of the geometry of the vessel 120 (e.g., whether a bending radius has been encountered). In some embodiments, an external image of the vessel 120 (e.g., radiographic image, such as angiographic image, fluoroscopic image, a computed tomography image, and/or other suitable image) is used to determine whether an occlusion 246 is present or the nature of the geometry of the vessel 120.

It will be appreciated that the stiffness of the intravascular ultrasound imaging system 100 may also be adjusted using the embodiment of the rigidity modulating catheter 202 as described with respect to FIG. 4 in similar manner as described with respect to step 530.

Although the device and system has been exemplarily disclosed as intraluminal device, the invention can be applied to other interventional devices that are crossing the lumens of the vessels for providing access to other vessel (e.g. for bypass). Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:
1. An elongate device for insertion into a body lumen of a patient, the elongate device comprising:
  a compressible elongate member comprising a proximal portion and a distal portion;

a pair of filars extending within the compressible elongate member and affixed to the compressible elongate member;

a fixed member;

a biasing member which is spaced from the fixed member and configured to control a compressive pressure applied to the pair of filars;

wherein the filars of the pair of filars are configured to extend through the fixed member and are secured to the biasing member; and wherein the filars of the pair of filars are configured to adjust a stiffness of the compressible elongate member while the compressible elongate member is disposed within the body lumen of the patient; and a spring disposed at an end of the compressible elongate member and disposed between the fixed member and the biasing member; and an imaging element disposed at the distal portion of the compressible elongate member and configured to obtain an intraluminal data associated with the body lumen.

2. The device of claim 1, wherein the pair of filars is configured to maintain a neutral position of the compressible elongate member upon changing its stiffness.

3. The device of claim 1, wherein the compressible elongate member comprises a lumen extending from the distal portion to the proximal portion.

4. The device of claim 3, wherein the filars are disposed within the lumen of the compressible elongate member.

5. The device of claim 4, wherein the filars of the pair of filars extends through the spring.

6. The device of claim 4, wherein the spring is coupled to the biasing member.

7. The device of claim 6, wherein the biasing member is operable to translate axially relative to the compressible elongate member.

8. The device of claim 1, wherein the fixed member, the biasing member, and the filars of the pair of filars are configured to reduce the stiffness of the compressible elongate member when the biasing member is in a first position.

9. The device of claim 8, wherein the biasing member is configured to maintain the stiffness of the compressible elongate member at predetermined values.

10. The device of claim 1, wherein the biasing member is configured to increase the stiffness of the compressible elongate member when the biasing member is in a second position.

11. The device of claim 1, wherein the imaging element comprises an intravascular ultrasound (IVUS) transducer.

12. The device of claim 1, wherein the compressible elongate member comprises a catheter.

13. A method, comprising:

positioning an elongate device within an anatomy of a patient, the elongate device having a longitudinal axis and comprising a plurality of filars extending along the longitudinal axis through elongate device and coupled to the elongate device, a stiffness modulator being disposed at a proximal end of the elongate device outside of the anatomy of the patient when the elongate device is positioned within the anatomy of the patient, the stiffness modulator including a fixed member, and a biasing member to which the plurality of filars are coupled under tension, the biasing member being spaced from the fixed member, wherein the plurality of filars are configured to extend through the fixed member and are secured to the biasing member; and with the elongate device positioned within the anatomy of the patient, adjusting a flexibility of the elongate device by adjusting a longitudinal position of the biasing member to which the filars are coupled relative to the fixed member to adjust the tension of the filars which are coupled to the elongate devicei wherein the stiffness modulator further includes a spring disposed at an end of the elongate member and disposed between the fixed member and the biasing member; and an imaging element disposed at a distal portion of the elongate member and configured to obtain an intraluminal data associated with the anatomy.

14. The method of claim 13, further comprising:

obtaining measurement data associated with the anatomy using a sensor of the elongate device.

15. The method of claim 13 wherein the adjusting comprises:

increasing the flexibility of the elongate device by moving the biasing member toward the fixed member to reduce the tension of the plurality of filars which are coupled to the elongate device.

16. The method of claim 15, wherein the adjusting further comprises:

decreasing the flexibility of the elongate device by moving the biasing member away from the fixed member to increase the tension of the plurality of filars which are coupled to the elongate device.

17. The method of claim 13, wherein the adjusting comprises applying a compressive force to the spring.

18. The method of claim 13, wherein the adjusting comprises applying a tensile force to the spring.

19. A catheter comprising:

an elongate member configured to be inserted into a body lumen of a patient, the elongate member comprising a proximal portion and a distal portion;

a stiffening mechanism coupled to the elongate member and configured to change the stiffness of the elongate member during a medical procedure;

wherein the stiffening mechanism comprises:

a tensioning member comprising a plurality of filars extending along a longitudinal axis of the elongate member and coupled to the elongate member; and a stiffness modulator fixedly coupled to the tensioning member and disposed at the proximal portion of the elongate member, the stiffness modulator including a fixed member, and a biasing member to which the plurality of filars are coupled under tension, the biasing member being spaced from the fixed member, the biasing member being movable relative to the fixed member to change the stiffness of the elongate member by adjusting the tension of the plurality of filars which are coupled to the elongate member, wherein the plurality of filars are configured to extend through the fixed member and are secured to the biasing member;

a spring disposed at an end of the elongate member and disposed between the fixed member and the biasing member; and an imaging element disposed at the distal portion of the elongate member and configured to obtain an intraluminal data associated with the body lumen.

* * * * *